United States Patent
Ito (10) Patent No.: US 10,827,920 B2
(45) Date of Patent: Nov. 10, 2020

(54) OCT APPARATUS

(71) Applicant: NIDEK CO., LTD., Aichi (JP)

(72) Inventor: Koichi Ito, Aichi (JP)

(73) Assignee: NIDEK CO., LTD., Aichi (JP)

( * ) Notice: Subject to any disclaimer, the term of this patent is extended or adjusted under 35 U.S.C. 154(b) by 111 days.

(21) Appl. No.: 16/052,017

(22) Filed: Aug. 1, 2018

(65) Prior Publication Data

US 2019/0038127 A1 Feb. 7, 2019

(30) Foreign Application Priority Data

Aug. 3, 2017 (JP) .................................. 2017-151154

(51) Int. Cl.
*A61B 3/10* (2006.01)
*A61B 3/00* (2006.01)
*A61B 3/12* (2006.01)

(52) U.S. Cl.
CPC ............ *A61B 3/102* (2013.01); *A61B 3/0025* (2013.01); *A61B 3/12* (2013.01)

(58) Field of Classification Search
CPC .......... A61B 3/102; A61B 3/0025; A61B 3/12
USPC ........................................ 351/200, 205, 206
See application file for complete search history.

(56) References Cited

U.S. PATENT DOCUMENTS

| | | | | |
|---|---|---|---|---|
| 8,514,404 | B2 * | 8/2013 | Podoleanu ........... | A61B 5/0066 356/497 |
| 9,279,659 | B2 * | 3/2016 | Izatt ........................ | A61B 3/102 |
| 2017/0332898 | A1 | 11/2017 | Uji et al. | |
| 2018/0353063 | A1 | 12/2018 | Uji et al. | |

FOREIGN PATENT DOCUMENTS

| | | |
|---|---|---|
| EP | 2 901 919 A1 | 8/2015 |
| JP | 2016-123467 A | 7/2016 |
| WO | 2011111376 A1 | 9/2011 |
| WO | 2016/111248 A1 | 7/2016 |
| WO | 2016/111379 A1 | 7/2016 |

OTHER PUBLICATIONS

Communication dated Jan. 21, 2019, issued by the European Patent Office in counterpart European Application No. 18186977.7.
Communication dated May 10, 2019, from the European Patent Office in counterpart European Application No. 18186977.7.

* cited by examiner

*Primary Examiner* — Tuyen Tra
(74) *Attorney, Agent, or Firm* — Sughrue Mion, PLLC (57) ABSTRACT

An OCT apparatus includes an OCT optical system, a processor that processes a signal from the OCT optical system, and a light guiding optical system disposed on a measurement light path of the OCT optical system. The light guiding optical system forms a pivot point, at which a measurement light turns based on motion of an optical scanner deflecting the measurement light, in an anterior portion of a subject eye, and guides the measurement light passed through the pivot point to a fundus. The OCT optical system includes a compensation unit that compensates for an amount of change in a light path length of the measurement light path between a state in which an angle-of-view switching optical system is inserted and a state in which the angle-of-view switching optical system is retracted.

13 Claims, 3 Drawing Sheets

Fig. 3

OCT APPARATUS

CROSS-REFERENCE TO RELATED APPLICATION

This application claims priority from Japanese Patent Application No. 2017-151154 filed on Aug. 3, 2017, the entire subject-matter of which is incorporated herein by reference.

TECHNICAL FIELD

This disclosure relates to an OCT apparatus that obtains OCT data of a fundus of a subject eye.

BACKGROUND

As an OCT apparatus that obtains OCT data of a subject, there has been known an apparatus that is capable of processing a spectral interference signal output from an OCT optical system and acquiring OCT data, for example. In recent years, there has been proposed an apparatus for acquiring a wide-angle tomographic image.

For example, JP-A-2016-123467 discloses an apparatus including an apparatus main body having an optical system that scans a fundus, in which an attachment optical system is inserted between the apparatus main body and a subject eye, and thereby a scanning range of measurement light is more expanded on the fundus than during retraction (during non-insertion) of the attachment optical system.

According to the technology disclosed in JP-A-2016-123467, an optical configuration of the optical system that is used for performing good scanning of the measurement light in a wide range of the fundus is disclosed; however, the present inventor has found through a study that it is difficult to achieve good acquisition of wide-angle OCT data only by the configuration, and there are several technical problems.

SUMMARY

An object of this disclosure is to provide an OCT apparatus that is capable of acquiring wide-angle OCT data favorably.

(1) There is provided an OCT apparatus including:
an OCT optical system that has a light splitter splitting light from an OCT light source light traveling to a measurement light path and light traveling to a reference light path, and a detector detecting an interference signal of measurement light guided onto a fundus of a subject eye via the measurement light path and reference light from the reference light path;
an image processor that is capable of processing a spectral interference signal output from the OCT optical system to acquire OCT data; and
a light guiding optical system that is an optical system disposed on the measurement light path, that has an optical scanner deflecting the measurement light from the light splitter, that forms a pivot point, at which the measurement light turns based on motion of the optical scanner, in an anterior portion of the subject eye, and that guides the measurement light passed through the pivot point to the fundus,
in which the light guiding optical system is capable of switching to either an insertion state in which an angle-of-view switching optical system is inserted into the light guiding optical system or a retraction state in which the angle-of-view switching optical system is retracted from the light guiding optical system, a size of an angle of view indicating a scanning range of the measurement light on the fundus in the insertion state is different from a size of the angle of view in the retraction state, and
the OCT optical system includes compensation unit that compensates for an amount of change in a light path length of the measurement light path between the insertion state and the retraction state.

(2) In the OCT apparatus according to the above (1), the angle-of-view switching optical system increases the angle of view such that the measurement light is guided to a wide-angle region including a fundus center area and a fundus peripheral area in one transverse direction in which the measurement light traverses the fundus in the insertion state, with respect to the retraction state.

(3) In the OCT apparatus according to the above (2), the light guiding optical system includes an objective optical system forming a first pivot point, at which the measurement light turns, at a conjugated position with the optical scanner, and
the angle-of-view switching optical system is inserted into and removed from between the objective optical system and the subject eye, and further forms a second pivot point by turning the measurement light passed through the first pivot point toward an optical axis.

(4) In the OCT apparatus according to the above (1), the angle-of-view switching optical system has a light path length that is longer than an equivalent length to an ocular axial length in the subject eye, and
the compensation unit compensates for the amount of change equivalent to the light path length of the angle-of-view switching optical system.

(5) In the OCT apparatus according to the above (1), the compensation unit changes a light path length between the light splitter and the optical scanner on the measurement light path of the OCT optical system to compensate for the amount of change.

(6) In the OCT apparatus according to the above (1), the compensation unit switches a light path length of the reference light path, to which the reference light is guided from the light splitter, between a first light path length corresponding to a light path length of the measurement light path in the retraction state and a second light path length corresponding to a light path length of the measurement light path in the insertion state, on the reference light path of the OCT optical system.

(7) In the OCT apparatus according to the above (1), the compensation unit includes a light path branching portion that causes at least a part of the reference light path of the OCT optical system, and forms a first branched light path having a first light path length corresponding to a light path length of the measurement light path in the retraction state and a second branched light path having a second light path length corresponding to a light path length of the measurement light path in the insertion state.

(8) In the OCT apparatus according to the above (7), the compensation unit includes a switch unit selectively guiding the reference light from the light splitter to one of the first branched light path and the second branched light path.

(9) In the OCT apparatus according to the above (7), the OCT optical system simultaneously guides the reference light from the light splitter to the first branched light path and the second branched light path, and
the detector simultaneously detects the interference signal by the reference light from the first branched light path and the interference signal by the reference light from the second branched light path.

(10) In the OCT apparatus according to the above (1), the compensation unit includes a drive unit that is driven in order to compensate for the amount of change, and the OCT apparatus further includes a controller that controls the drive unit according to an insertion and a retraction of the angle-of-view switching optical system.

(11) The OCT apparatus according to the above (1) further includes:

a dispersion correcting unit that corrects a dispersion amount of an optical system between the measurement light path and the reference light path in an optical manner, in a signal processing manner, or in both of the manners, in which a first correction value for correcting the dispersion amount in the retraction state and a second correction value for correcting the dispersion amount in the insertion state are set at each different value.

(12) In the OCT apparatus according to the above (11), the angle-of-view switching optical system increases the angle of view such that the measurement light is guided to a wide-angle region including a fundus center area and a fundus peripheral area in one transverse direction in which the measurement light traverses the fundus in the insertion state, and the second correction values are set at each different value for at least the fundus center area and the fundus peripheral area.

(13) In the OCT apparatus according to the above (1), the OCT optical system includes:

a light-flux diameter changer that changes a light-flux diameter between the light splitter and the optical scanner; and a controller that corrects a change in a spot size of the measurement light on the fundus between the insertion state and the retraction state by controlling the light-flux diameter changer.

According to the OCT apparatus of this disclosure, it is possible to acquire wide-angle OCT data at a good signal strength.

DETAILED DESCRIPTION

Figure 1:
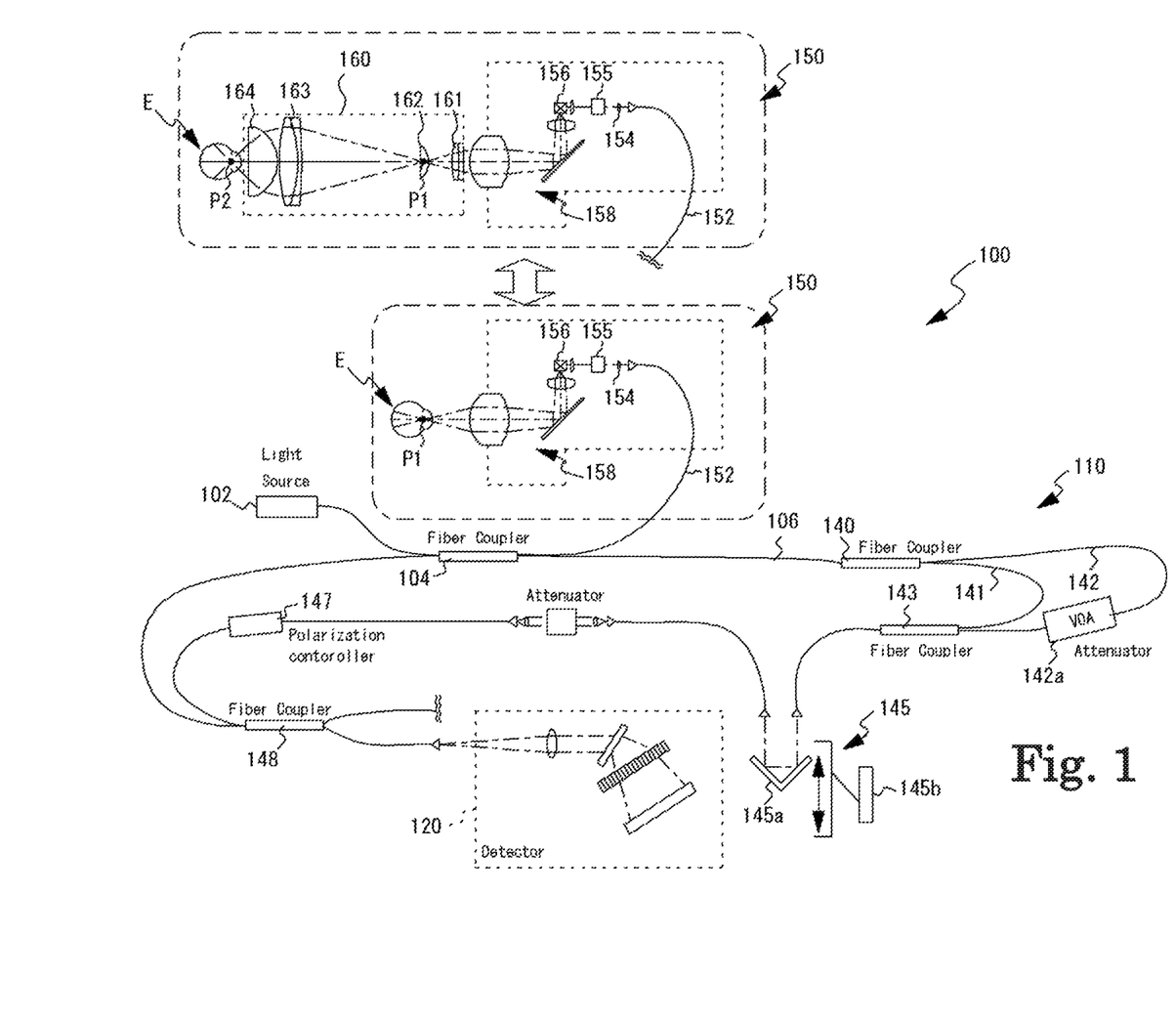
FIG. 1 is a diagram showing an example of an optical system of an OCT apparatus according to an example.
Figure 2:
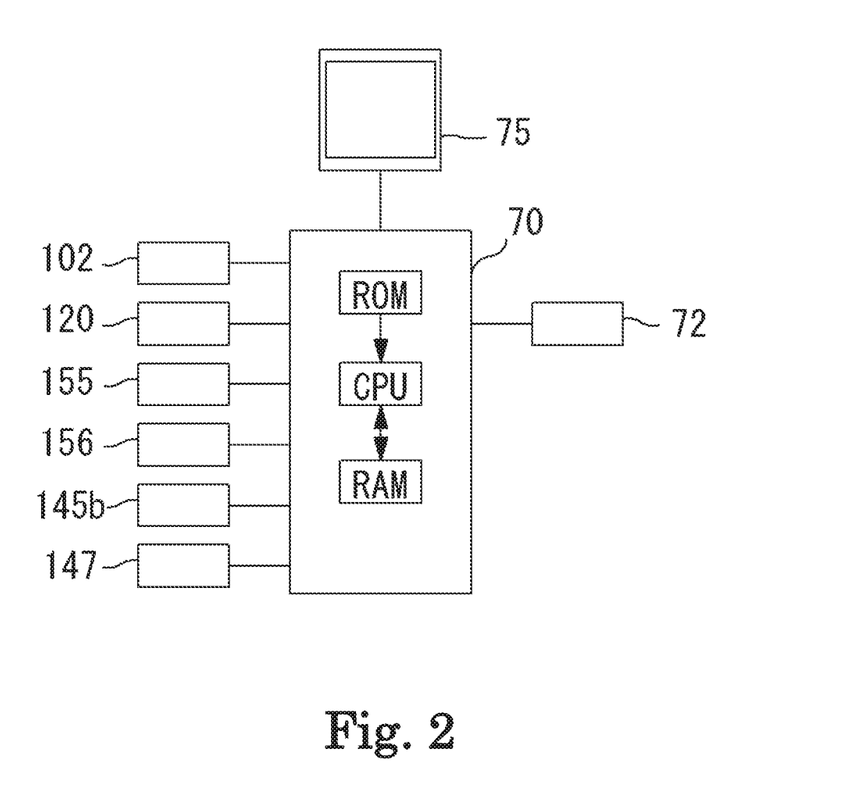
FIG. 2 is a diagram showing an example of a control system of the OCT apparatus according to the example.
Figure 3:
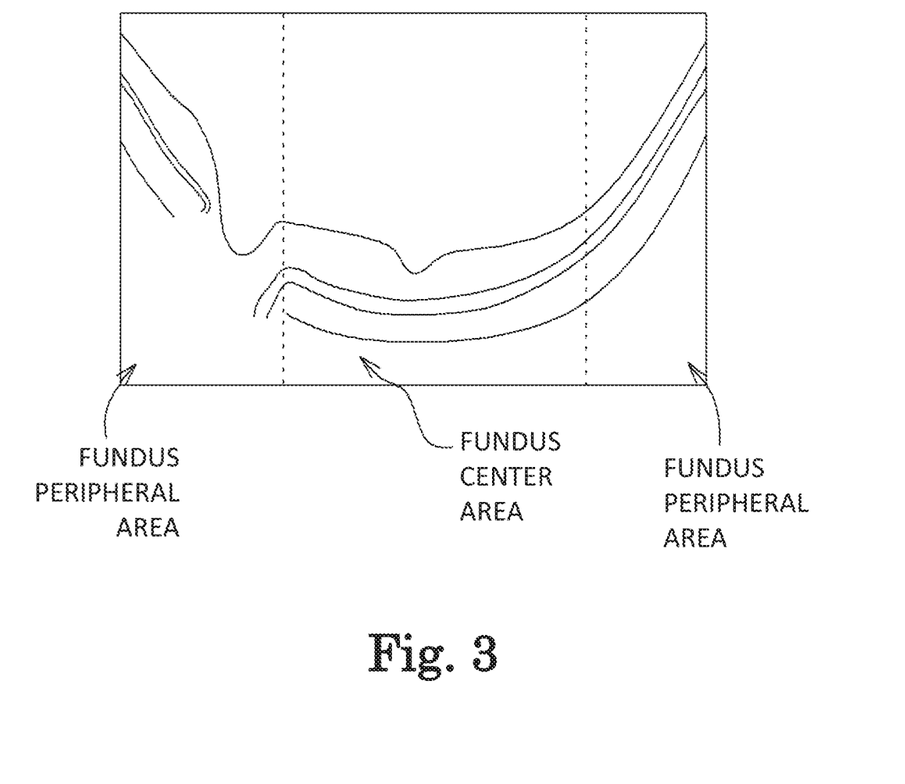
FIG. 3 is a diagram showing an example of a B scan image of a fundus imaged in an insertion state.

An example of an embodiment of this disclosure will be described with reference to the figures. FIGS. 1 to 3 are diagrams showing an example of the embodiment. The following chapters classified by < > are used individually or in association with each other.

An OCT apparatus according to the embodiment may include an OCT optical system and may be capable of processing a spectral interference signal output from a detector of the OCT optical system and acquiring OCT data. In this case, the OCT optical system may be a Fourier domain OCT optical system (an SS-OCT optical system or an SD-OCT optical system), for example. The OCT optical system may have a light splitter for splitting light from an OCT light source to light traveling to a measurement light path and light traveling to a reference light path and may detect the spectral interference signal of measurement light guided via the measurement light path to a subject and reference light from the reference light path.

In addition, the OCT apparatus may include an image processor, and the image processor may be capable of processing a spectral interference signal output from the OCT optical system and acquiring the OCT data.

<Wide-Angle Imaging of Fundus>

For example, the OCT optical system may have a light splitter, which splits light from an OCT light source to light traveling to the measurement light path and light traveling to the reference light path, and a detector, which detects an interference signal of the measurement light guided to a fundus of a subject eye via the measurement light path and the reference light from the reference light path.

The OCT optical system may be an OCT optical system that is capable of guiding the measurement light to a wide-angle region. The wide-angle region includes a fundus center area and a fundus peripheral area in one transverse direction in which the measurement light traverses the fundus. For example, in a case where the measurement light traverses the fundus in a specific transverse direction (for example, a horizontal direction), the wide-angle region may a region at a wide angle so as to traverse both of the fundus center area and the fundus peripheral area. In addition, regarding a transverse region that the measurement light traverses, a transverse region in the fundus center area and a transverse region in the fundus peripheral area may be continuous to each other in the transverse direction, for example. For example, a region having a length of 18 mm or longer on the fundus may be set as the wide-angle region. It is needless to say that the wide-angle region may be used in a case of obtaining a region narrower than 18 mm. The apparatus of the embodiment is used particularly in a case of imaging a peripheral region of a subject eye of which a fundus has a large degree of curvature.

For example, at least a region including a macular region and an optic nerve head of the fundus may be set as the fundus center area, and a region including both regions on outer sides from both end portions of the fundus center area in one transverse direction may be set as the fundus peripheral area. It is needless to say that setting is not limited to this, and at least a region including the macular region of the fundus may be set as the fundus center area, and a region including both regions on outer sides from both end portions of the fundus center area in one transverse direction may be set as the fundus peripheral area, for example.

For example, the OCT optical system that is capable of guiding the measurement light to the wide-angle region of the fundus may include an objective lens optical system or may include an objective mirror optical system using a concave mirror. In addition, in the OCT optical system, an attachment optical system is attached to (inserted into) the objective lens optical system, and thereby the measurement light is guided to the wide-angle region.

Hereinafter, a case where an angle-of-view switching optical system can be inserted into and removed from a light guiding optical system disposed on the measurement light path, and a size of an angle of view, which indicates a scanning range of the measurement light on the fundus is different between an insertion state and a retraction state will be described. In this case, in the embodiment, the size of the angle of view is more increased in the insertion state than in the retraction state. It is needless to say that the size is not limited thereto, and the size of the angle of view may be more decreased in the insertion state than in the retraction state.

The light guiding optical system is formed on the measurement light path. The light guiding optical system includes at least an optical scanning unit (optical scanner) and may further include an objective optical system. The optical scanner deflects the measurement light from the light splitter, and thereby the light guiding optical system forms a pivot point, at which the measurement light turns based on motion of the optical scanner, in an anterior portion of a subject eye and guides the measurement light passed through the pivot point to the fundus. Scanning of the measurement light about the pivot point on the fundus is performed in accordance with the motion of the optical scanner.

The objective optical system is an optical system that is disposed between the optical scanner of the light guiding optical system and the subject eye and is used for forming the pivot point. The pivot point is formed at a conjugated position of the optical scanner with respect to the objective optical system. The pivot point is also referred to as a "first pivot point". The objective optical system may be a refraction system including a lens, a reflection system including a mirror, or a combination of both of the systems.

The angle-of-view switching optical system is inserted into and removed from the light guiding optical system on the measurement light path. In this specification, a state in which the angle-of-view switching optical system is inserted into the light guiding optical system is referred to as an "insertion state", and a state in which the angle-of-view switching optical system is retracted from the light guiding optical system is referred to as a "retraction state". The size of the angle of view, which indicates a scanning range of the measurement light on the fundus, in the insertion state may be different from that in the retraction state. For convenience of description, unless otherwise noted, the angle-of-view switching optical system includes at least one lens in the following description.

Hereinafter, a state in which the angle of view is increased in the insertion state in which the angle-of-view switching optical system is inserted into the light guiding optical system is described. In this case, in the insertion state of the angle-of-view switching optical system, the angle of view is increased from the retraction state such that the measurement light is guided to the wide-angle region of the fundus.

The angle-of-view switching optical system may be inserted and may be removed from between the objective optical system included in the light guiding optical system and the subject eye. In this case, it is more preferable to have a lens disposition of a lens position of the angle-of-view switching optical system, in which a lens having principal power in the angle-of-view switching optical system is disposed to be inserted and removed from between the first pivot point and the subject eye. In the case of the disposition, it is easy to secure a longer operation distance than that in a case where the lens having the principal power is disposed between the objective optical system and the first pivot point.

In a case where the lens having the principal power in the angle-of-view switching optical system is inserted between the first pivot point and the subject eye, the angle-of-view switching optical system relays the first pivot point in the insertion state and forms a second pivot point. Specifically, the angle-of-view switching optical system forms the second pivot point by turning the measurement light passed through the first pivot point toward an optical axis in the insertion state. In the insertion state, the second pivot point is positioned in an anterior portion of the subject eye, and thereby scanning of the measurement light is performed on the fundus.

In this disclosure, a size of the scanning range of the measurement light on the fundus is described as an "angle of view". Here, the "angle of view" more depends on performance of an optical system that is disposed on the subject eye than the optical scanner and is a value obtained by assuming that the optical scanner is appropriately operated such that a maximum angle of view is realized.

<Compensation for Change in Light Path Length Difference>

When the angle-of-view switching optical system is inserted into and removed from the light guiding optical system, a light path length of the measurement light path is changed, and thus there can be found a light path length difference between the reference light and the measurement light. For example, since the angle-of-view switching optical system, which relays the pivot point formed by the objective optical system, is likely to be large in size and is likely to have a long light path length, the change in the light path length difference according to the insertion and the retraction is also considered to be increased. For example, there has been known a technology in which an attachment optical system is installed on an inspection window of fundus imaging OCT such that it is possible to image an anterior portion (for example, see "JP-A-2011-147612" or the like by the present applicant). In such an apparatus, a light path length of the measurement light path is changed before and after the attachment optical system is attached and detached. However, in the apparatus described above, the light path length of the attachment optical system is short, and an imaged site is switched to the anterior portion. In this manner, the light path length of the measurement light path in an ocular bulb is short, and thus a sufficient compensation length in the apparatus was about an ocular axial length ($\cong$32 mm). By comparison, the light path length of the angle-of-view switching optical system in the embodiment is longer than the ocular axial length. For example, in the embodiment, it is necessary to compensate for an amount of change by about three to eight times an equivalent length to the ocular axial length in some cases. For example, in an example of design of the angle-of-view switching optical system that switches an angle of view from about 60° to about 100° in an OCT apparatus that is capable of performing imaging at the angle of view of about 60°, the light path length of the angle-of-view switching optical system was about 170 mm. In this manner, there is no configuration in the related art which is capable of coping with a change in the light path length of the measurement light path according to the insertion and the retraction of the angle-of-view switching optical system.

The OCT optical system may include a compensation unit that compensates for an amount of change in the light path length of the measurement light path between the insertion state and the retraction state.

The OCT optical system may include a plurality of reference light paths as the compensation unit. For example, the reference light path may branch to at least two paths of a first branched light path and a second branched light path. Here, the first branched light path has a first light path length corresponding to a light path length of the measurement light path in the retraction state. In addition, the second branched light path has a second light path length corresponding to a light path length of the measurement light path in the insertion state. A light path length difference between the first branched light path and the second branched light path may be determined in advance. Specifically, the light path length difference may be a length that is substantially equal to the light path length of the angle-of-view switching optical system.

The OCT optical system may cause the detector to simultaneously detect both of the interference signal due to the reference light from the first branched light path and an interference signal due to the reference light from the second branched light path or selectively detect any one of the two interference signals.

The reference lights from the light splitter are simultaneously guided to the first branched light path and the second branched light path, and thereby the interference signals due to the reference lights from both of the light paths of the first branched light path and the second branched light path can be simultaneously detected by the detector. However, in this case, a light path length difference between the measurement light and the reference light through the first branched light path and a light path length difference between the measurement light and the reference light through the second branched light path are replaced between "substantially 0" and "substantially a light path length of the angle-of-view switching optical system" based on the insertion and retraction of the angle-of-view switching optical system. Therefore, strength of one interference signal corresponding to a state (insertion state/retraction state) of the light guiding optical system of the two types of interference signals having a different path of the reference light path from each other is obviously stronger than that of the remaining one. In a case where the light path length of the angle-of-view switching optical system is sufficiently long, the interference signal of the remaining one has a level of strength which does not cause a problem. In the retraction state, the interference signal by the reference light through the first branched light path is a signal having a signal strength that is stronger than that of the interference signal by the reference light through the second branched light path, and vice versa in the insertion state. The light from the OCT light source is split to the measurement light and the reference light by the light splitter; however, it is not essential for a side of the reference light path to have an element such as the subject eye, which significantly attenuates a beam. Therefore, even when the first branched light path and the second branched light path which branch from the reference light path are formed, sufficient intensity is secured to obtain the interference signal on both of the branched light paths. Therefore, even in a configuration in which either light path length of the measurement light path or the reference light path is switched according to the insertion and the retraction of the angle-of-view switching optical system, it is possible to perform good acquisition of the OCT data based on the interference signal detected by the detector.

The OCT optical system may have, as a part of the compensation unit, a switch (an example of a drive unit) that switches the light path, through which the reference light is guided from the light splitter, between the first branched light path and the second branched light path. Consequently, the detector can selectively detect one of the interference signal by the reference light from the first branched light path and the interference signal by the reference light from the second branched light path. For example, a controller of the OCT apparatus may cause the switch to perform switching depending on the state (insertion state/retraction state) of the light guiding optical system. In other words, the switch may be controlled to be driven such that the reference light from the light splitter is guided to the first branched light path in the retraction state, and the reference light from the light splitter is guided to the second branched light path in the insertion state. A method of compensating for an amount of change in the light path length on the measurement light path is considered to be particularly advantageous in a case where the light path length of the angle-of-view switching optical system is relatively short or the like, compared with a system without the switch.

In addition, the reference light path branching as described above is not absolutely necessary to be provided. In this case, the compensation unit may adjust at least one length of the measurement light path and the reference light path, for example. For example, in a case where the compensation unit adjusts the light path length of the reference light path, the compensation unit may switch the light path length of the reference light path, to which the reference light is guided from the light splitter, between the first light path length corresponding to the light path length of the measurement light path in the retraction state and the second light path length corresponding to the light path length of the measurement light path in the insertion state. In addition, in a case where the compensation unit adjusts the light path length of the measurement light path, the compensation unit may change a light path length between the light splitter and the optical scanner on the measurement light path, thereby compensating for an amount of change in the light path length according to the insertion and the retraction of the angle-of-view switching optical system described above.

<Dispersion Correction>

In addition, the OCT apparatus of the embodiment includes a dispersion correcting unit (dispersion compensating unit) that corrects (compensates for) a dispersion amount in an optical system between the measurement light path and the reference light path, thereby being capable of obtaining good OCT data. The dispersion correcting unit may correct the dispersion amount optically or may correct in a signal processing manner (including at least one of signal processing or calculation). In a case of the former, the dispersion correcting unit is an element of the OCT optical system. In a case of the latter, the dispersion correcting unit is an electronic circuit (may be a dedicated circuit or an image processor) which is connected to the detector.

Incidentally, in the embodiment, the angle-of-view switching optical system is inserted into or removed from the light guiding optical system, and thereby the dispersion amount in the optical system between the measurement light path and the reference light path is likely to be changed. In the OCT apparatus of the embodiment, a plurality of different correction values of the dispersion amount may be set in the dispersion correcting unit. At least a first correction value for correcting a dispersion amount in the retraction state and a second correction value for correcting the dispersion amount in the insertion state are set, and thereby it is possible to acquire good OCT data in both cases where the angle-of-view switching optical system is inserted and removed.

In addition, the correction value of the dispersion correcting unit may be further subdivided. For example, since the dispersion amount in the optical system between the measurement light path and the reference light path can vary for each scanning angle of the optical scanner, the first correction value, the second correction value, or both correction values may be set as different values for each scanning angle of the optical scanner. In particular, in a case where a scanning range is performed at a wide angle in the insertion state of the angle-of-view switching optical system, a case of having a significant difference between a dispersion amount related to measurement light, with which the fundus center area is irradiated, and a dispersion amount related to measurement light, with which the fundus peripheral area is irradiated, is considered. In the OCT apparatus of the embodiment, a different correction value may be set for each of at least the fundus center area and the fundus peripheral area.

<Light-flux Diameter Changer>

In addition, in the OCT apparatus of the embodiment, the angle-of-view switching optical system is inserted into the light guiding optical system, and thereby a light-flux diameter of the measurement light is considered to be increased. In this case, a spot size of the measurement light on the fundus increases as a light-flux diameter increases in the insertion state, and thereby image resolving power is considered to be more degraded, compared with the retraction state. In this respect, the OCT apparatus of the embodiment includes a light-flux diameter changer. Here, the light-flux diameter changer adjusts a light-flux diameter of the measurement light with which the subject eye is irradiated. The controller (processor) of the OCT apparatus causes the light-flux diameter changer to switch the light-flux diameter in association with a state (insertion state/retraction state) of the light guiding optical system, and thereby it is possible to change the image resolving power before and after the angle-of-view switching optical system is inserted and removed. More specifically, in a case where the state is switched from the retraction state to the insertion state, the controller drives the light-flux diameter changer such that the light-flux diameter of the measurement light decreases. In addition, in a case where the state is switched from the insertion state to the retraction state, the light-flux diameter changer is driven such that the light-flux diameter of the measurement light increases. Consequently, the change in spot size of the measurement light is corrected. Since the spot size is substantially proportional to an angle of view, it is preferable to drive the light-flux diameter changer by a correction amount in association with a ratio of the angle of view (scanning range) between the insertion state and the retraction state. For example, the light-flux diameter changer may be a variable beam expander.

Example

Hereinafter, an optical coherence tomography (OCT) apparatus shown in FIGS. 1 and 2 will be described as an example. For example, the OCT apparatus according to the example has spectral domain OCT (SD-OCT) as a basic configuration.

An OCT apparatus 1 includes a light source 102, an interference optical system (OCT optical system) 100, and a calculation controller (calculation control unit) 70 (refer to FIG. 2). Additionally, in the OCT apparatus, a memory 72, a display unit 75, a front image observing system and a fixation target projecting system (not shown) may further be provided. The calculation controller (hereinafter, a controller) 70 is connected to the light source 102, the interference optical system 100, the memory 72, and the display unit 75.

The interference optical system 100 guides the measurement light to an eye E by a light guiding optical system 150. The interference optical system 100 guides the reference light to a reference optical system 110. The interference optical system 100 causes a detector (light receiving element) 120 to receive an interference signal light that is acquired due to interference of the reference light with the measurement light reflected from the eye E. The interference optical system 100 is mounted in a housing (apparatus main body) (not shown), and the housing moves three-dimensionally with respect to the eye E by a known alignment moving mechanism via an operation unit such as a joystick. In this manner, alignment may be performed with respect to the subject eye.

The SD-OCT type may be used for the interference optical system 100. A light source that emits a light-flux having a short coherence length is used as the light source 102, and a spectroscopic detector that performs spectroscopic dispersion and detects a spectral interference signal for each wavelength component is used as the detector 120.

A coupler (splitter) 104 is used as a first light splitter and splits the light emitted from the light source 102 to light traveling to the measurement light path and light traveling to the reference light path. For example, the coupler (fiber coupler) 104 guides the light from the light source 102 to an optical fiber 152 on a side of the measurement light path and guides the light to a coupler (fiber coupler) 140 on a side of the reference light path via a fiber 106. Consequently, the light from the light source 102 is guided to the reference optical system 110.

<Light Guiding Optical System>

The light guiding optical system 150 is provided to guide the measurement light to the eye E. For example, in the light guiding optical system 150, the optical fiber 152, a collimator lens 154, a variable beam expander 155, an optical scanner 156, and an objective lens system 158 (the objective optical system in the example) are provided in this order. In this case, the measurement light is emitted from an emission end of the optical fiber 152 and becomes a parallel beam by the collimator lens 154. Then, the light travels toward the optical scanner 156 in a state of having a desired light-flux diameter by the variable beam expander 155. The eye E is irradiated with the beam passing through the optical scanner 156 via the objective lens system 158. A first pivot point P1 is formed at a conjugated position of the optical scanner 156 with respect to the objective lens system 158. The anterior portion is positioned at the pivot point P1, and thereby the measurement light reaches the fundus without eclipse. In addition, the fundus is scanned with the measurement light depending on the operation of the optical scanner 156. In this case, the measurement light is scattered•reflected by tissue of the fundus.

The optical scanner 156 may scan the eye E with the measurement light in XY directions (transverse directions). For example, the optical scanner 156 is configured of two galvano mirrors, and a reflection angle of the mirror is adjusted optionally by a driving mechanism. A reflection (traveling) direction of the light-flux emitted from the light source 102 changes, and the fundus is scanned in any optional direction. For example, as the optical scanner 156, an acousto-optic modulator (AOM) or the like that changes the traveling (deflection) direction of light may be used, in addition to a reflective mirror (a galvano mirror, a polygon mirror, or a resonant scanner).

Scattered light (reflected light) of the measurement light from the eye E travels back via a path used during light projection, is incident to the optical fiber 152, and reaches the coupler 104. The coupler 104 guides the light from the optical fiber 152 to a light path toward the detector 120.

<Attachment Optical System>

An attachment optical system 160 (an example of the "angle-of-view switching optical system") in the OCT apparatus according to the example is inserted and removed from between the objective optical system 158 in the light guiding optical system 150 and the subject eye E. A lens tube including the attachment optical system is attached to and detached from a housing surface (not shown), and thereby the attachment optical system 160 is inserted and removed from between the objective optical system 158 and the subject eye E.

The attachment optical system 160 may include a plurality of lenses 161 to 164. Here, a lens having principal power in the attachment optical system 160 shown in FIG. 1 is the lens 164 placed in front of the subject eye. An insertion/retraction position of at least the lens 164 is between the first pivot point P1 that is formed by the objective optical system 158 and the subject eye E. At least the lens 164 turns the measurement light passed through the first pivot point P1 toward an optical axis L, and thereby a second pivot point P2 is formed at a conjugated position of the optical scanner 156 with regard to the attachment optical system 160 the objective optical system 158. In other words, the attachment optical system 160 is an optical system that relays the pivot point P1 to the pivot point P2.

In the example, a solid angle of the measurement light at the second pivot point P2 is larger than a solid angle at the first pivot point P1. For example, the solid angle at the second pivot point P2 is increased as twice or more as the solid angle at the first pivot point P1. In the example, it is possible to perform scanning at an angle of view of about 60° in the retraction state, and it is possible to perform scanning at an angle of view of about 100° in the insertion state.

The variable beam expander 155 is the light-flux diameter adjusting unit in the example. As an example, the variable beam expander 155 may include a plurality of lenses that form a both-side telecentric optical system and may be configured to switch a light-flux diameter by changing a lens space by an actuator. The variable beam expander 155 adjusts the light-flux diameter of the measurement light based on an instruction from the controller 70.

If the light-flux diameter of the measurement light that is guided from the variable beam expander 155 to the optical scanner 156 is constant between the insertion state and the retraction state, the spot size of the measurement light is proportional to the angle of view on the fundus. Therefore, the resolving power is more degraded in the insertion state than in the retraction state. In the example, the controller 70 drives the variable beam expander 155 according to the insertion and the retraction of the attachment optical system and more decreases the light-flux diameter in the insertion state than in the retraction state. A rate of the light-flux diameters (light-flux diameters in the variable beam expander 155) in the insertion state and the retraction state is inversely proportional to the angle of view in the insertion state and the retraction state, and thereby it is possible to suppress a change in resolving power based on the insertion and retraction of the attachment optical system 160.

Incidentally, in order to secure a sufficient operation distance, the attachment optical system 160 needs to cause the measurement light to be tuned from a position having a sufficient light beam height toward the optical axis L. In addition, in order to suppress an aberration caused by the attachment optical system 160 within a permissible range, power of the lenses included in the attachment optical system 160 is limited. Hence, it is difficult to shorten the light path length of the attachment optical system 160.

Although there is an OCT apparatus in the related art that is configured to adjust the light path length difference between the reference light and the measurement light, there is no OCT apparatus that has an adjustment range that is applicable to the insertion and retraction of the attachment optical system 160. For example, in the related art, there has been known a technology in which an optical adapter is installed such that it is possible to perform imaging an anterior portion in fundus imaging OCT (for example, see "JP-A-2011-147612" or the like by the present applicant). However, the optical adapter does not relay the pivot point formed by an optical system of an apparatus main body, and there is no demand for a wide-angle scanning range. Therefore, the optical adapter can be formed to have a relatively short light path length. Further, a position of an image surface is changed from the fundus to the anterior portion in response to insertion of the optical adapter. Hence, there is no need to significantly adjust the light path length difference in response to the insertion of the optical adapter.

<Reference Optical System>

The reference optical system 110 generates the reference light that is combined with fundus reflection light of the measurement light. The reference light passing through the reference optical system 110 is coupled and interferes with light from the measurement light path by a coupler (Fiber coupler) 148. The reference optical system 110 may be one of a Michelson type or a Mach-Zehnder type.

The reference optical system 110 shown in FIG. 1 is formed by a transmission optical system. In this case, the reference optical system 110 does not cause the light from the coupler 104 to return but transmits the light, thereby guiding the light to the detector 120. The reference optical system 110 is not limited thereto and may be formed by a reflection optical system and guide the light from the coupler 104 to the detector 120 by causing the light to be reflected from the reflection optical system, for example.

In the example, the reference optical system 110 may have a plurality of reference light paths. For example, in FIG. 1, the coupler (fiber coupler) 140 causes the reference light path to branch to a light path (the first branched light path in the example) via which a fiber 141 passes and a light path (the second branched light path in the example) via which a fiber 142 passes. The fiber 141 and the fiber 142 are connected to a coupler (fiber coupler) 143. Consequently, two branched light paths are coupled, and light is incident to the coupler 148 via a light path length difference adjusting unit 145 and a polarization controller 147.

In the example, the reference light from the coupler 104 is simultaneously guided to the fiber 141 and the fiber 142 by the coupler 143. Light passing through either the fiber 141 or the fiber 142 is coupled with the measurement light (fundus reflection light) in the coupler 148.

A light path length difference between the fiber 141 and the fiber 142, that is, a light path length difference between the first branched light path and the second branched light path, may be a fixed value. In the example, the light path length difference is set to be substantially equal to the light path length of the attachment optical system 160.

An optical member for adjusting the light path length difference between the measurement light and the reference light may be disposed on at least any one of the measurement light path and the reference light path. As an example, the reference light path adjusting unit 145 is provided in the optical system shown in FIG. 1, and a mirror 145a having two orthogonal surfaces is provided at a corresponding position so as to control the light path length difference between the measurement light and the reference light. The mirror 145a moves in an arrow direction by an actuator 145b, and thereby it is possible to increase and decrease the light path length of the reference light path. It is needless to say that a configuration, in which the light path length difference between the measurement light and the reference light is adjusted, is not limited thereto. For example, in the light guiding optical system 150, the collimator lens 154 and a coupler 153 move integrally, and thereby the light path length of the measurement light is adjusted. As a result, the light path length difference between the measurement light and the reference light may be adjusted.

Here, In the example, since the reference light path adjusting unit 145 is provided on a light path between the coupler 143 and the coupler 148, that is, on a common light path between the first branched light path and the second branched light path, it is possible to perform adjustment of an ocular axial length with regard to an individual difference, which is the adjustment of the light path length difference between the measurement light path and the reference light path, with respect to both of the first branched light path and the second branched light path.

It is preferable that an adjustment range of the light path length in the reference light path adjusting unit 145 is set to be sufficiently shorter than the light path length difference between the fiber 141 and the fiber 142 (in other words, the light path length difference between the first branched light path and the second branched light path).

<Attenuator>

In addition, in an example of FIG. 1, the fiber 142 is connected to an attenuator 142a (attenuation unit). The attenuator 142a is disposed to adjust an intensity balance between the measurement light and the reference light in the insertion state and the retraction state of the attachment optical system 160. As shown in FIG. 1, in a case where the attenuator 142a is disposed on a branched light path in the reference optical system, an attenuation rate of the attenuator 142a is constant.

In addition, the attenuator 142a may be disposed at a position other than the branched light path in the reference optical system. In this case, the attenuation rate in the attenuator may be variable or switched by the controller 70 between the insertion state and the retraction state of the attachment optical system 160.

<Correction of Manufacturing Tolerance of Zero-delay Position>

Incidentally, a zero-delay position (a position at which the light path length difference between the measurement light path and the reference light path is zero) is considered to be different for each device of the attachment optical system 160 due to a manufacturing tolerance of the attachment optical system 160 and the fiber 142. For example, the manufacturing tolerance can be corrected by adjusting an initial distance value of a distance between the collimating lens 154 and a diopter correcting lens in the light guiding optical system 150. The OCT apparatus 1 may include an adjusting mechanism (not shown) for adjusting such a manufacturing error. The adjusting mechanism may be configured to be capable of performing adjustment after a product delivery of the OCT apparatus 1.

<Light Detector>

The detector 120 is provided to detect interference of the light from the measurement light path with the light from the reference light path. In the example, the detector 120 is a spectroscopic detector and includes an optical spectrometer and a line sensor, for example, in which the measurement light and the reference light which are coupled by the coupler 148 are scattered by the optical spectrometer and are received in a different region (pixel) of the line sensor for each wavelength. Consequently, an output for each pixel is acquired as a spectral interference signal.

Since a curvature of the fundus does not necessarily match an image forming surface of the measurement light, and a displacement between both of a fundus center area and a fundus peripheral area increases in at least one of the areas in the insertion state of the attachment optical system 150, it is preferable to secure a sufficient depth range in the light detector in consideration of the displacement. For example, in the SD-OCT, it is preferable to provide a line camera having a sufficient number of pixels with respect to an anticipated depth range. In addition, the following configuration may be further employed as "modification examples".

<Acquisition of Depth Information>

The controller 70 performs processing (Fourier analysis) on a spectral signal detected by the detector 120 and obtains OCT data of the subject eye.

The spectral signal (spectral data) may be rewritten as a function of a wavelength $\lambda$ and may be converted to an equal interval function I (k) with regard to a wave number k ($=2\pi/\lambda$). Alternatively, the spectral signal may be acquired as an equal interval function I (k) with regard to the wave number k from the beginning (a k-clock technology). The calculation controller may perform Fourier transform of the spectral signal in a space having the wave number k, thereby obtaining OCT data in a depth (Z) region.

Further, information after the Fourier transform may be obtained as a signal containing a real component and an imaginary component in a Z space. The controller 70 may obtain absolute values of the real component and the imaginary component in the signal in the Z space, thereby acquiring the OCT data.

Here, in the coupler 148, the reference light passing through the first branched light path and the reference light passing through the second branched light path are simultaneously guided and each is coupled to the measurement light. Since a large light path length difference, which is substantially equal to the light path length of the attachment optical system 160, occurs between the first branched light path and the second branched light path, one of the reference light passing through the first branched light path and the reference light passing through the second branched light path is likely to interfere with the measurement light; however, the other reference light is unlikely to interfere with the measurement light. Although the spectral interference signal from the detector 120 contains a component due to the reference light passing through the first branched light path and a component due to the reference light passing through the second branched light path, one of the two types of components according to the state of the light guiding optical system 150 is obtained as a remarkably stronger signal than the other. As a result, it is possible to obtain good OCT data regardless of the state of the light guiding optical system 150. In other words, the OCT apparatus according to the example has the light path length difference corresponding to the attachment optical system 160 and includes the plurality of reference light paths, and thereby the amount of change according to the insertion and the retraction of the attachment optical system 160, which is the amount of change in the light path length difference on the measurement light path, is compensated regardless of the state of the light guiding optical system 150.

The reference light path adjusting unit 145 needs to be controlled to adjust the light path length difference related to the ocular axial length of the subject eye E, which is the light path length difference between the measurement light path and the reference light path, in advance. For example, in the example, the mirror 145a may be moved in a predetermined adjustment range, an interference signal may be acquired at each position, and the position of the mirror 145a may be determined on the basis of a position, at which the strength of the interference signal has the highest strength. In a case where the adjustment range of the light path length in the reference light path adjusting unit 145 is sufficiently small with respect to the light path length difference between the first branched light path and the second branched light path, at a position in the adjustment range of the reference light path adjusting unit 145, at which the interference signal has a strength peak, can be uniquely identified.

Since the fundus reflection light of the measurement light from the fundus peripheral area is weaker than the reflected light from the fundus center area in the insertion state, the light path length difference between the measurement light path and the reference light path may be adjusted by the reference light path adjusting unit 145 such that the zero-delay position between the measurement light path and the reference light path overlaps anticipated fundus tissue (for example, the retina, the choroid, the sclera, or the like) in the fundus peripheral area.

In the example, a difference in dispersion amount in the optical system between the measurement light path and the reference light path is corrected in a signal processing manner. Specifically, the correction value stored in a memory in advance is applied in processing of the spectral signal, and thereby the correction is performed. In the example, a first correction value corresponding to the retraction state and a second correction value which is a value different from the first correction value and corresponds to the insertion state are stored in a memory 72 in advance, and a correction value to be applied is switched according to the state of the light guiding optical system 150. As a result, in the OCT apparatus according to the example, an amount of change according to the insertion and retraction of the attachment optical system 160, which is an amount of change in the dispersion amount between the measurement light path and the reference light path, is compensated in each state of the light guiding optical system 150.

Further, in the example, a plurality of second correction values corresponding to the insertion state are set depending on scanning positions of the measurement light. Specifically, a correction value for the fundus center area and a correction value for the fundus peripheral area are set as second correction values which are different from each other. For example, the first correction value may be applied to a region within an angle of 60° of the fundus, and the second correction value may be set as a value that is applied to a region apart from the region at the angle of 60° Since the attachment optical system 160 has significant power, overall, a significant difference in dispersion amount is considered to occur between a light-flux passing through the fundus center area and a light-flux passing through the fundus peripheral area. By comparison, in the example, since the correction value of the dispersion amount changes depending on an irradiation position of the fundus with the measurement light, it is possible to obtain good OCT data in the wide-angle region of the fundus.

It is needless to say that the second correction value may be further subdivided. For example, the entire fundus is divided into the fundus center area, a first fundus peripheral area on an outer side from the fundus center area, and a second fundus peripheral area on an outer side from the first fundus peripheral area, and a correction value corresponding to the fundus center area, a correction value corresponding to the first fundus peripheral area, and a correction value corresponding to the second fundus peripheral area may be set to be different from each other as the second correction value.

<Control System>

The controller 70 may include a CPU (processor), a RAM, a ROM, and the like (refer to FIG. 2). For example, the CPU of the controller 70 may control the OCT apparatus. The RAM stores various types of information temporarily. For example, in the ROM of the controller 70, various programs for controlling operations of the OCT apparatus, the initial value, or the like may be stored.

The non-volatile memory (hereinafter, simply abbreviated to "memory") 72 as a storage unit, the display unit 75, and the like are electrically connected to the controller 70. A non-transitory storage medium, which is capable of storing the storage content even when an electric power supply is cut off, may be used for the memory 72. For example, a hard disk drive, a flash ROM, a USB memory that is removably installed in the OCT apparatus or the like can be used as the memory 72. The memory 72 may store a control program for controlling the acquisition of the OCT data and the imaging of an OCT image. In addition, the memory 72 may store various types of information related to imaging other than the OCT image generated from the OCT data. The display unit 75 may display the OCT image generated from the OCT data.

An insertion/retraction detector that automatically detects whether or not the attachment optical system 160 is inserted into the light guiding optical system may be provided, and the controller may perform control or processing of each member of the OCT optical system 100 based on a detection signal from the detector. For example, switching control of the light-flux diameter by the variable beam expander 155, setting control of the zero-delay position by the reference light path adjusting unit 145, change processing of the dispersion amount in the optical system between the measurement light path and the reference light path, or the like may be appropriately performed as described above. The insertion detector may be a sensor disposed in the vicinity of the objective optical system 158.

It is needless to say that an examiner may input information that identifies the state of the light guiding optical system (the insertion state/retraction state of the attachment optical system) on a user interface (UI) of the OCT apparatus, and thereby the controller may perform the control and the processing of each member in the OCT optical system 100 based on the corresponding information.

Modification Examples

<Forming of Plurality of Reference Light Paths Corresponding to Insertion State>

In the above description, one reference light path corresponding to the insertion state of the angle-of-view switching optical system is set; however, the number of reference light paths is not limited thereto, and a plurality of reference light paths may be set. Specifically, the OCT optical system may have, as the reference light paths corresponding to the insertion state, a first reference light path having a light path length set for obtaining the OCT data including the fundus center area and a second reference light path which has a light path length set for obtaining the OCT data including the fundus peripheral area and is different from the first reference light path. In a case where a reference light path corresponding to each state of the light guiding optical system (here, to each of two types of states of the insertion state and the retraction state of the angle-of-view switching optical system), three or more reference light paths are provided in the OCT optical system.

The light path length difference between the first reference light path and the second reference light path may be set to correspond to a light path length difference between the measurement lights between the fundus center area and the fundus peripheral area. For example, in consideration of the curvature of the ocular bulb, a light path length of the second reference light path may be set to be shorter than a light path length of the first reference light path.

In this case, the image processor may obtain OCT data including the fundus center area based on an interference signal of the measurement light guided to the fundus center area and the reference light from the first reference light path or may obtain OCT data including the fundus peripheral area based on an interference signal of the measurement light guided to the fundus peripheral area and the reference light from the second reference light path, for example. In this case, the OCT data including the fundus center area and the OCT data including the fundus peripheral area may be continuous to at least one in the transverse direction and a depth direction, for example.

In this manner, the reference light path corresponding to the fundus center area and the reference light path corresponding to the fundus peripheral area are set, and thereby it is possible to acquire the OCT data in the wide-angle region at a good signal strength, for example.

The image processor may combine the OCT data including the fundus center area and the OCT data including the fundus peripheral area and may obtain wide-angle OCT data of the fundus of the subject eye. Consequently, it is possible to obtain one item of the wide-angle OCT data.

In this case, the optical scanner may scan the fundus with the measurement light in one scanning direction, thereby scanning the wide-angle region including the fundus center area and the fundus peripheral area. In this case, a scanned region in the fundus center area and a scanned region in the fundus peripheral area may be continuous to each other in the transverse direction, for example. In addition, the optical scanner may be configured to scan the wide-angle region on the fundus with the measurement light to a scannable scan angle, for example. In addition, the optical scanner may be disposed substantially at a conjugated position with the pupil of the subject eye and may measure the measurement light with the pupil center as the pivot point, for example.

In a case where the optical scanner is provided, a wide-angle region including the fundus center area and the fundus peripheral area may be scanned with the measurement light by B scan once by the optical scanner, and the OCT data including the fundus center area and the OCT data including the fundus peripheral area may be acquired. Consequently, it is possible to smoothly acquire the OCT data in the wide-angle region, for example.

For example, the OCT optical system may include a first detector corresponding to the fundus center area and a second detector corresponding to the fundus peripheral area. In this case, the first detector is used for detecting an interference signal of the measurement light guided to the fundus center area with the reference light from the first reference light path. In addition, the second detector is a detector different from the first detector and is used for detecting an interference signal of the measurement light guided to the fundus peripheral area with the reference light from the second reference light path. In such a configuration, for example, it is possible to use the first detector and the second detector in parallel. As the result, it is possible to reliably detect both items of OCT data of the fundus center area and the fundus peripheral area, and it is possible to smoothly acquire both items of OCT data at a good signal strength.

In the embodiment, a case where two reference light paths are each provided to correspond to the fundus center area and the fundus peripheral area is described; however, the number of reference light paths is not limited thereto, and three or more reference light paths may be provided. As an example, a case where the entire fundus is divided into three areas of the fundus center area, the first fundus peripheral area, and the second fundus peripheral area is described. The first fundus peripheral area is disposed on the outer side from the fundus center area, and the second fundus peripheral area is disposed on the outer side more from the first fundus peripheral area.

In this case, the first reference light path corresponding to the fundus center area, a second reference light path corresponding to the first fundus peripheral area, and a third reference light path corresponding to the second fundus peripheral area may be provided in the OCT optical system, for example.

In addition, light path lengths of the two reference light paths may be controlled such that the optical system may be caused to switch between a first wide-angle imaging mode and a second wide-angle imaging mode. For example, in the first wide-angle imaging mode, a light path length in the first reference light path is set to correspond to the fundus center area, and a light path length in the second reference light path is set to correspond to the first fundus peripheral area. On the other hand, in the second wide-angle imaging mode, the light path length in the first reference light path is set to correspond to the fundus center area or the first fundus peripheral area, and the light path length in the second reference light path is set to correspond to the second fundus peripheral area.

<Angle-of-View Switching Optical System by Reflection System (Mirror System)>

In the embodiment, a case where the angle-of-view switching optical system includes at least one lens is described; however, the system is not necessarily limited thereto. The angle-of-view switching optical system may be a mirror system (mirror group). More specifically, the angle-of-view switching optical system may be a decentered mirror system (mirror group) having one or more mirrors. Even in this case, since the light path length in the measurement light path changes according to the insertion and retraction of the angle-of-view switching optical system, the light path length is effectively compensated by the compensation unit.

In the above description, the example of the SD-OCT is described; however, the example is not limited thereto, and the example may be applied to SS-OCT.

In the above description, the OCT apparatus for imaging the subject eye is exemplified; however, the OCT apparatus is not limited thereto, and the embodiment may be applied to an OCT apparatus for imaging OCT data of the subject. The subject is not limited to an eye (an anterior portion, a fundus, or the like). The subject may be a living organism such as skin or a material other than the living organism.

What is claimed is:
1. An OCT apparatus comprising:
an OCT optical system that has a light splitter splitting light from an OCT light source to light traveling to a measurement light path and light traveling to a reference light path, and a detector detecting an interference signal of measurement light guided onto a fundus of a subject eye via the measurement light path and reference light from the reference light path;

an image processor that is capable of processing a spectral interference signal output from the OCT optical system to acquire OCT data; and a light guiding optical system that is an optical system disposed on the measurement light path, that has an optical scanner deflecting the measurement light from the light splitter, that forms a pivot point, at which the measurement light turns based on motion of the optical scanner, in an anterior portion of the subject eye, and that guides the measurement light passed through the pivot point to the fundus, wherein the light guiding optical system is capable of switching to either an insertion state in which an angle-of-view switching optical system is inserted into the light guiding optical system or a retraction state in which the angle-of-view switching optical system is retracted from the light guiding optical system, a size of an angle of view indicating a scanning range of the measurement light on the fundus in the insertion state is different from a size of the angle of view in the retraction state, the OCT optical system includes a compensation unit that compensates for an amount of change in a light path length of the measurement light path between the insertion state and the retraction state; and wherein the compensation unit includes a light path branching portion that causes at least a part of the reference light path of the OCT optical system, and forms a first branched light path having a first light path length corresponding to a light path length of the measurement light path in the retraction state and a second branched light path having a second light path length corresponding to a light path length of the measurement light path in the insertion state.

2. The OCT apparatus according to claim 1,
wherein the angle-of-view switching optical system increases the angle of view such that the measurement light is guided to a wide-angle region including a fundus center area and a fundus peripheral area in one transverse direction in which the measurement light traverses the fundus in the insertion state, with respect to the retraction state.

3. The OCT apparatus according to claim 2,
wherein the light guiding optical system includes an objective optical system forming a first pivot point, at which the measurement light turns, at a conjugated position with the optical scanner, and
the angle-of-view switching optical system is inserted into and removed from between the objective optical system and the subject eye, and further forms a second pivot point by turning the measurement light passed through the first pivot point toward an optical axis.

4. The OCT apparatus according to claim 1,
wherein the angle-of-view switching optical system has a light path length that is longer than an equivalent length to an ocular axial length in the subject eye, and
the compensation unit compensates for the amount of change equivalent to the light path length of the angle-of-view switching optical system.

5. The OCT apparatus according to claim 1,
wherein the compensation unit switches a light path length of the reference light path, to which the reference light is guided from the light splitter, between a first light path length corresponding to a light path length of the measurement light path in the retraction state and a second light path length corresponding to a light path length of the measurement light path in the insertion state, on the reference light path of the OCT optical system.

6. The OCT apparatus according to claim 1,
wherein the compensation unit includes a switch unit selectively guiding the reference light from the light splitter to one of the first branched light path and the second branched light path.

7. The OCT apparatus according to claim 1,
wherein the OCT optical system simultaneously guides the reference light from the light splitter to the first branched light path and the second branched light path, and
the detector simultaneously detects the interference signal by the reference light from the first branched light path and the interference signal by the reference light from the second branched light path.

8. The OCT apparatus according to claim 1, further comprising:
a dispersion correcting unit that corrects a dispersion amount of an optical system between the measurement light path and the reference light path in an optical manner, in a signal processing manner, or in both of the manners,
wherein a first correction value for correcting the dispersion amount in the retraction state and a second correction value for correcting the dispersion amount in the insertion state are set at each different value.

9. The OCT apparatus according to claim 8,
wherein the angle-of-view switching optical system increases the angle of view such that the measurement light is guided to a wide-angle region including a fundus center area and a fundus peripheral area in one transverse direction in which the measurement light traverses the fundus in the insertion state, with respect to the retraction state, and
the second correction values are set at each different value for at least the fundus center area and the fundus peripheral area.

10. The OCT apparatus according to claim 1,
wherein the OCT optical system includes:
a light-flux diameter changer that changes a light-flux diameter between the light splitter and the optical scanner; and
a controller that corrects a change in a spot size of the measurement light on the fundus between the insertion state and the retraction state by controlling the light-flux diameter changer.

11. The OCT apparatus according to claim 1, wherein a light path length of a first fiber configuring a part of the first branched light path is different from a light path length of a second fiber configuring a part of the second branched light path.

12. The OCT apparatus according to claim 1, wherein the first branched light path and the second branched light path are coupled upstream from the detector.

13. The OCT apparatus according to claim 1, wherein a reference light path adjusting unit is provided on a common light path of the first branched light path and the second branched light path, the reference light path adjusting unit performing adjustment of an ocular axial length with regard to an individual difference.

* * * * *